United States Patent [19]
Siegel et al.

[11] Patent Number: 5,272,258
[45] Date of Patent: Dec. 21, 1993

[54] MONOCLONAL ANTIBODIES TO C-REACTIVE PROTEIN

[75] Inventors: Joan N. Siegel, Oak Park; Lawrence A. Potempa, Deerfield; Henry Gewurz, Evanston, all of Ill.

[73] Assignee: Rush-Presbyterian-St. Luke's Medical Center, Chicago, Ill.

[21] Appl. No.: 374,166

[22] Filed: Jun. 29, 1989

Related U.S. Application Data

[63] Continuation-in-part of Ser. No. 372,442, Dec. 7, 1989, abandoned.

[51] Int. Cl.$^5$ .................. C07K 15/28; C12N 5/12; G01N 33/53
[52] U.S. Cl. .................. 530/388.25; 435/240.27; 435/7.1
[58] Field of Search .............. 435/7, 240.27, 7.1, 435/7.2; 530/380, 387, 388.25

[56] References Cited

PUBLICATIONS

Baltz et al., *Ann. N.Y. Acad. Sci.*, 389, 49 (1982).
Bray, et al., *Journal of Immunology*, 140, 4271 (1988).
Bray, et al., *Clinical Immunology Newsletter*, 8, 137 (1987).
Chesebro and Metzger, *Biochemistry*, 11, 766 (1972).
Chu, et al., *Proceedings Amer. Assoc. Cancer Res.*, 29, 371a (1988).
Chudwin, *J. Allergy Clin. Immunol.*, 77, 2169 (1986).
Deodhar et al., *Cancer Research*, 42, 5084 (1982).
Dougherty, et al., *Protides of the Biological Fluids*, 34, 291 (1986).
Gewurz, *Hospital Practice*, 17, 67 (1982).
Gotschlich and Edelman, *Proc. Natl. Acad. Sci.*, 57, 706 (1967).
Gupta, et al., *Arthritis and Rheumatism*, 31, R39 (1988).
Hirai, et al., *Protides of the Biological Fluids*, 34, (1986), pp. 283–286.
Kaplan and Volanakis, *Journal of Immunology*, 112, 2135 (1974).
Kearney et al., *Immunological Communications*, 11, 275 (1982).
Kennett, et al., *Monoclonal Antibodies, Hybridomas A New Dimension In Biological Analysis*, (1980), p. 363.
Kilpatrick and Volanakis, *Journal of Immunology*, 134, 3364 (1985).
Kilpatrick, et al., *Molecular Immunology*, 19, 1159 (1982).
Kinoshita, et al., *Biochemistry*, 28, 9840 (1989).
Kinoshita, et al., *The FASEB Journal*, 2, A1149 (1988).
Laemmli, *Nature*, 227, 680 (1970).
Lai, et al., *Journal of Biological Chemistry*, 260, 13377 (1985).
Lindner and Robey, *Int. J. Peptide Protein Res.*, 30, 794 (1987).
Maudsley and Pepys, *Immunology*, 62, 17 (1987).
Mantzouranis, et al., *Pediatric Research*, 18, 260A (1984).
Mold et al., *J. Exp. Med.*, 154, 1703 (1981).
Mortensen, et al., *Journal of Immunology*, 117, 774 (1976).
Nakayama, et al., *Journal of Immunology*, 128, 2435 (1982).
Nakayama, et al., *Journal of Immunology*, 132, 1336 (1984).
Nguyen, et al., *Journal of Biological Chemistry*, 261, 10450 (1986).
Nilsson, *Int. Arch. Allergy*, 32, 35 (1967).
Osmand, et al., *Proc. Natl. Acad. Sci.*, 74, 1214 (1977).
Potempa, et al., *Inflammation*, 12, 391 (1988).

(List continued on next page.)

Primary Examiner—Christina Chan
Assistant Examiner—Susan A. Loring
Attorney, Agent, or Firm—Willian Brinks Olds Hofer Gilson & Lione

[57] ABSTRACT

The invention comprises monoclonal antibodies reactive with native C-reactive protein (CRP) and modified CRP having the specificities described herein. The invention also comprises the hybridomas used to produce these antibodies. The antibodies may be used to detect or quantitate native CRP and modified CRP, and kits for performing such assays are part of the invention.

16 Claims, 4 Drawing Sheets

PUBLICATIONS

Potempa, et al., *Molecular Immunology*, 24, 531 (1987).
Potempa, et al., *Protides of the Biological Fluids*, 34, (1986), pp. 287–290.
Potempa, et al., *Molecular Immunology*, 20, 1165, (1983).
Rees, et al., *Clinical Research*, 37, 559A (1989).
Rees, et al., *Clinical Immunology and Immunopathology*, 48, 95 (1988).
Robey, et al., *Journal of Biological Chemistry*, 262, 7053 (1987).
Roux, et al., *Journal of Immunology*, 131, 2411 (1983).
Samberg, et al., *Cellular Immunology*, 116, 86 (1988).
Samols, *Biochem. J.*, 227, 759 (1985).
Siegel, et al., *J. Exp. Med.*, 140, 631 (1974).
Taggart and Samloff, *Science*, 219, 1228 (1983).
Tseng, et al., *Hybridoma*, 7, 185 (1988).
Tseng and Mortensen, *Molecular Immunology*, 25, 679 (1988).
Volanakis and Kaplan, *Proc. Soc. Exp. Biol. Med.*, 136, 612 (1971).
Volanakis and Kearney, *J. Exp. Med.*, 153, 1604 (1981).
Woo, et al., *Journal of Biological Chemistry*, 260, 13384 (1985).
Ying, et al., *Journal of Immunology*, 143, 221 (1989).
Ying, et al., *FASEB Journal*, 3, 1345a (1989).
Young and Williams, *Journal of Immunology*, 121, (1978).
Zeller, et al., *J. Lab. Clin. Med.*, 108, 567 (1986).
Zeller, et al., *Journal of Leukocyte Biology*, 40, 769 (1986).
Zhang, et al., *Journal of Immunology*, 138, 575 (1987).
Gewurz et al., *Adv. Intern. Med.*, 27, 345–72 (1982).
Gewurz, *Hospital Practice*, 67–81 (Jun. 1982).
Kilpatrick et al., *Molecular Immunology*, 19, 1159–65 (1982).
Tseng et al., *Hybridoma*, 7, 185–191 (1988).
Potempa et al., *J. Allergy Clin. Immunol.*, 77, 135a (1986).
Kinoshita et al., *Seventy Second Annual Meeting of the Federation Am. Soc. for Exp. Biol.*, J2, A 1149 (1988).
Iturralde and Coll, *Revista Espanola de Fisiologia*, 40, 279–88 (1984).
Ying et al., *FASEB J.*, 3, A1345 (1989).
Ying et al., *J. Immunol.*, 143, 221–228 (1989).
Tseng, J. et al. 1988 (Apr.), Monoclonal Antibodies to Human C-Reactive Protein . . . Hybridoma 7 185.
Kilkpatrick et al., 1982, Demonstration of Calcium-Induced Conformational Changes, Mol. Immunol. 19 1159.

MONOCLONAL ANTIBODIES TO C-REACTIVE PROTEIN

This application is a continuation in part of application Ser. No. 07/372,442, filed Jun. 27, 1989, now abandoned for "Monoclonal Antibodies To C-Reactive Protein."

BACKGROUND OF THE INVENTION

C-reactive protein (CRP) is a prototype acute phase protein which increases dramatically in concentration in the blood during the first 24-48 hours of tissue necrosis and inflammation, Gewurz, *Hospital Practice*, 17, 67 (1982), and tests that measure CRP are used clinically to monitor the course of inflammatory reactions. CRP and/or CRP complexes can activate the complement system, Kaplan and Volanakis, *J.Immunol*, 112, 2135 (1974); Siegel et al., *J. Exp. Medicine*, 140, 631 (1974). They can also bind to and promote the activation of neutrophils and macrophages and enhance the respiratory burst response of these cells to certain stimuli in vitro. Mortensen et al., *J. Immunol.*, 117, 774 (1976); Kilpatrick and Volanakis, *J. Immunol.*, 134, 3364 (1985); Zeller et al., *J. Lab. Clin. Med.*, 108, 567 (1986); Zeller et al., *J. Leukocyte Biol.*, 40, 769 (1986). CRP has the capacity to protect against pneumococcal infections, influence clearance reactions, modify antibody formation to certain antigens and inhibit the metastasis of certain tumors in the mouse in vivo. Mold et al., *J. Exp. Med.*, 154, 1703 (1981); Nakayama et al., *J. Immunol.* 128, 2435 (1982); Nakayama et al., *J. Immunol*, 54, 319 (1984); Deodhar et al., *Cancer Res.*, 42, 5084 (1982). These properties suggest a significant biological role for CRP.

Native CRP is a cyclic pentamer composed of five identical, noncovalently-associated subunits, with its prototypic binding reactivity directed to phosphorylcholine (PC)[5] in the presence of calcium. Volanakis and Kaplan, *Proc. Soc. Exp. Bio. Med.* 136, 612 (1971). Recently in Potempa et al., *Molec. Immunol.*, 20, 1165 (1983) and Potempa et al., *Molec Immunol*, 24, 531 (1987), a "neo-CRP" antigenicity was described. The neo-CRP antigenicity is expressed by native CRP modified by urea-chelation, acid treatment, heating, or direct immobilization on polystyrene plates The neo-CRP anti-genicty is also expressed on the intact CRP subunits and on the in vitro translation product of the CRP gene produced by hosts transformed with the gene by recombinant DNA techniques, rantzouranis et al., *Pediatric Res.* 18, 260a (1984).

The two molecular configurations of CRP can be distinguished antigenically, electrophoretically and by ligand binding reactivity. Potempa et al., *Molec. Immunol.*, 20, 1165 (1983) and Potempa et al., *Molec. Immunol.*, 24, 531 (1988). Polyclonal goat anti-native CRP reacted preferentially with both free and ligand-bound CRP in the presence of calcium (i.e., with native CRP epitopes), but showed no or minimal reactivity with CRP immobilized directly on solid phase surfaces or treated with urea, acid or heat in the absence of calcium. By contrast, polyclonal goat anti-neo-CRP showed preferential reactivity with CRP modified or immobilized in the absence of calcium (i.e., with neo-CRP epitopes) and little or no reactivity with CRP bound to ligands in the presence of calcium.

Forms of CRP expressing neo-CRP epitopes have the ability to activate and modulate the functional responses of platelets, polymorphonuclear leukocytes and monocytes, Potempa et al., *Inflammation.* 12, 391 (1988). Further, polyclonal antiserum to neo-CRP has been used to look for neo-CRP determinants in serum and tissue. Neo-CRP antigenicity has been found on the surface of human natural killer (NK) cells and B lymphocytes, Bray et al., *J. Immunol*, 140, 4271 (1988), as well as in human skeletal muscle tissue, Rees et al., *Clin. Res.*, 37, 559a (1989). Potempa et al., *Molec. Immunol.*, 24, 531 (1987) described neo-CRP reactivity in the serum or plasma of patients with rheumatoid arthritis. Rees et al., *Clin. Immunol Immunopathol*, 48, 95 (1988) demonstrated neo-CRP reactivities in frozen sections of acute phase but not normal rabbit liver and in necrotic but not normal rabbit muscle. The presence of neo-CRP determinants in acute phase liver was interpreted to result from de novo synthesis of the CRF subunit, since primary translation products of both human CRP (Mantzouranis et al., *Pediatric Res.*, 18, 260a (1984)) and rabbit CRP (Samols et al., *Biochem J.*, 227, 759 (1985)) had been shown to precipitate with a polyclonal antibody specific for neo-CRP epitopes. The expression of neo-CRP epitopes in necrotic tissue was attributed to in situ acute phase modification of the CRP molecule. These properties suggest a significant biological role for neo-CRP, as well as native CRP.

Additional articles describing neo-CRP and its properties include: Potempa et al, *Protides of the Biological Fluids* 34, 287 (1986); Bray et al., *Clin. Immunol. Newsletter*, 8, 137 (1987); Samberg et al., *Cellular Immunology*, in press; Gupta et al., *Arthritis & Rheumatism* 31, R39a (1988); Chu et al., *Amer. Assoc. Cancer Res.*, 29, 371a (1988); Dougherty et al., *Protides of the Biological Fluids*, 34 291-93 (1986); and Chudwin et al., *J. Allergy Clin. Immunol.*, 77, 2169 (1986).

Monoclonal antibodies to CRP prepared using native CRP as the immunogen are known. See Kilpatrick et al., *Molec Immunol.*, 19, 1159 (1982); Tseng et al., *Hybridoma*, 7, 185 (1988); Kearney et al., *Immunol Communications*, 11, 275-82 (1982); Hirai et al., *Protides of the Biological Fluids* 34, 283 (1986); Tseng and Mortensen, *Molecular Immunology*, 25, 679 (1988); Roux et al., *J. Immunol.*, 131 2411-15 (1983); Volanakis and Kearney, *J. Exp. Med.*, 153, 1604 (1981). However, no reports describing monoclonal antibodies having the properties of the monoclonal antibodies of the present invention are known to Applicants. In particular, prior to the present invention, monoclonal antibodies reactive with modified CRP were not known.

SUMMARY OF THE INVENTION

Monoclonal antibodies ("mAbs") to human CRP have been prepared which react with either native CRP, modified CRP or both forms of the molecule. "Modified CRP" as used herein means CRP modified by immobilization on solid surfaces, heating, urea-chelation, sodium dodecyl sulfate treatment, acid treatment, other denaturation methods or other methods which can result in a conformational change in a protein. The term also means any form of CRP that expresses neo-CRP antigenicity.

The mAbs of the invention were divided into four groups according to their binding characteristics to various CRP preparations using a combination of ELISA, dot blot and Western blot assays. The CRP preparations used included: native CRP; CRP modified by immobilization on polystyrene plates, by urea-chelation and by sodium dodecyl sulfate treatment in the absence of calcium; intact CRP subunits; Pronase-digested CRP fragments; and CRP peptides. The mAbs were further characterized based upon their reactivity with CRP in the presence of calcium, their inhibition by phosphorylcholine (PC), their reactivity with serum amyloid P component and their reactivity with rabbit CRP.

The first group of mAb have the following specificities:

(a) they react with native human CRP;
(b) they do not react with modified human CRP;
(c) they do not react with intact human CRP subunit;
(d) they do not react with fragment A of Pronase-digested human CRP;
(e) they do not react with fragment B of Pronase-digested human CRP;
(f) they do not react with CRP peptides 1, 2, 3 or 4 (these peptides are described below); and
(g) they do not react with serum amyloid P component.

Further reactivities of the mAb of this first group define at least four epitopes on native human CRP: 1) a calcium-dependent, PC-inhibitable idiotype; 2) a calcium-dependent, non-PC-inhibitable epitope; 3) a calcium-influenced, EDTA-enhanced epitope; and 4) a calcium-independent epitope which also displays a unique cross reactivity with rabbit CRP.

The second group of mAb react with native human CRP and with modified human CRP, thus identifying a fifth native CRP epitope. These mAbs display significantly greater reactivity with native than with modified CRP. The mAb of this second group have the following additional specificities:

(a) they react with intact human CRP subunit;
(b) they do not react with fragment A of Pronase-digested human CRP;
(c) they do not react with fragment B of Pronase-digested human CRP;
(d) they recognize a calcium-independent epitope on native human CRP;
(e) their reactivity with native human CRP is not inhibited by PC;
(f) they do not react with CRP peptides 1, 2, 3 or 4;
(g) they react with modified rabbit CRP; and
(h) they do not react with serum amyloid P component.

The third group of mAb have the following specificities:

(a) they do not react with native human CRP;
(b) they react with modified human CRP;
(c) they react with intact human CRP subunit;
(d) they react with fragment A of Pronase-digested human CRP;
(e) they do not react with fragment B of Pronase-digested human CRP;
(f) they do not react with CRP peptides 1, 2, 3 or 4;
(g) they are not able to bind fluid phase native human CRP in the presence or absence of calcium;
(h) they do not react with serum amyloid P component.

Certain of the mAb of this third group have the further specificities:

(h) they react with modified rabbit CRP;
(i) they react with intact rabbit CRP sub-unit; (j) they react with fragment A of Pronase-digested rabbit CRP; and
(k) they do not react with fragment B of Pronase-digested rabbit CRP.

The fourth group of mAb have the following specificities:

(a) they do not react with native human CRP;
(b) they react with modified human CRP;
(c) they react with intact human CRP subunit;
(d) they do not react with fragment A of Pronase-digested human CRP;
(e) they react with fragment B of Pronase-digested human CRP;
(f) they do not react with CRP peptides 1, 2 or 3;
(g) they are not able to bind fluid phase native human CRP in the presence or absence of calcium;
(h) they do not react with serum amyloid P component.

Most of the fourth group of mAb also react with CRP peptide 4. This peptide is an octapeptide identical to the carboxyl-terminal sequence of human CRP.

Finally, certain of this fourth group of mAb have the following additional specificities:

(h) they react with modified rabbit CRP;
(i) they react with intact rabbit CRP subunit;
(j) they do not react with fragment A of Pronase-digested rabbit CRP; and
(k) they do react with fragment B of Pronase-digested rabbit CRP.

The invention also comprises hybridomas capable of producing mAbs having the specificities outlined above. The invention further provides immunoassays for detecting or quantitating native CRP or modified CRP comprising contacting the native CRP or modified CRP with a mAb of the invention having an appropriate specificity. Finally the invention provides kits for detecting or quantitating native CRP or modified CRP comprising a container of a mAb according to the invention having the proper specificity.

BRIEF DESCRIPTION OF THE DRAWINGS

FIGS. 1E and 1F show the reactivities of polyclonal goat antisera predominantly reactive with native- and neo-CRP epitopes, respectively.

DETAILED DESCRIPTION OF THE PRESENTLY PREFERRED EMBODIMENTS

Figure 1A:
FIGS. 1A-1F: Binding of mAb representative of each major group of mAb (the properties of which are further described below) by ELISA analysis to CRP captured by immobilized PC-KLH in the presence of calcium (●) and CRP directly immobilized in the absence of calcium () (FIGS. 1A-1D).
Figure 1B:
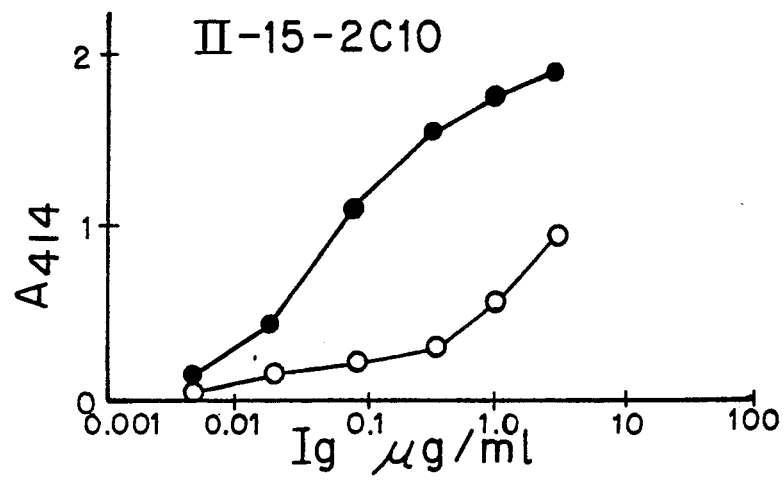
Figure 1C:
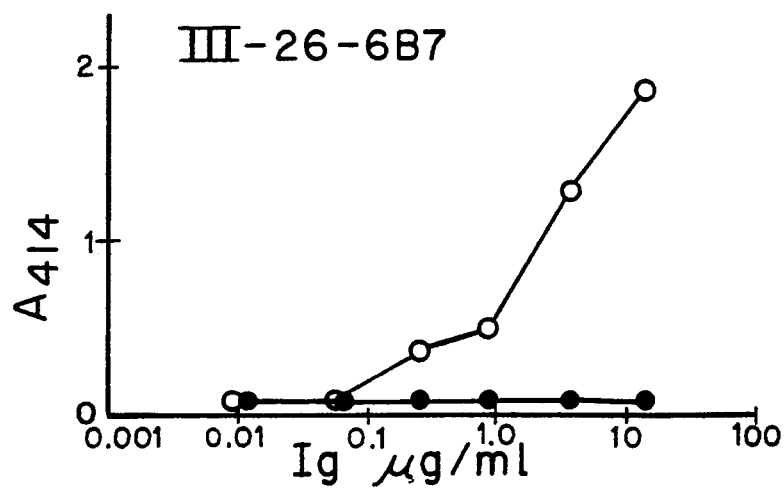
Figure 1D:
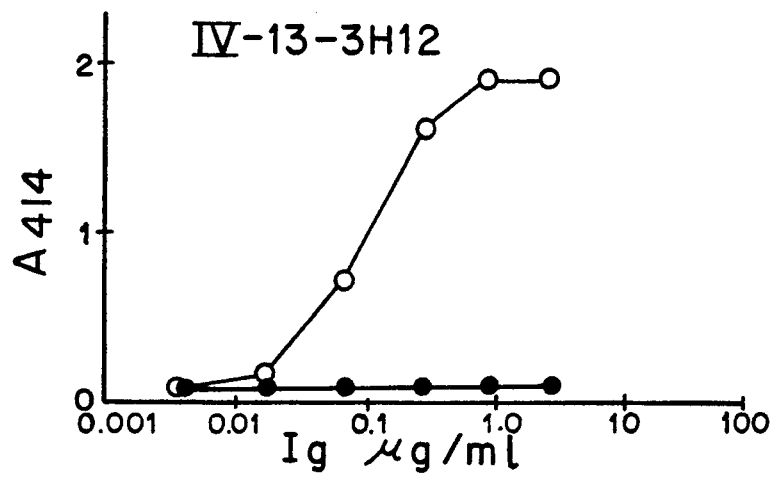

Techniques of preparing mAbs (mAb) are well known, and mAb to native CRP and modified CRP may be prepared using any of these known techniques. Briefly, immunoglobulin secreting cells from animals immunized with native CRP or modified CRP are fused to cells of an immortal cell line such as myeloma cells. The resultant hybrid cells ("hybridomas") are cloned and screened for the production of antibodies having the desired specificities.

The mAbs of the invention may be used in immunoassays to detect or quantitate native CRP and modified CRP. Any known immunoassay technique may be used, except that certain additional considerations are necessary when performing solid phase immunoassays for native CRP since immobilization of native CRP on a plastic solid surface results in modification of CRP. To overcome this problem, a ligand capture assay like those described in Example 2 below should be used when a solid phase assay for native CRP is desired.

Kits for detecting or quantitating native CRP or modified CRP are also part of the invention. A suitable kit comprises a container holding a mAb according to the present invention of the proper specificity. The mAb may be labeled or unlabeled.

Methods of using modified CRP and antibodies to modified CRP to detect or quantitate immune complexes and to remove aggregated immunoglobulins or immune complexes from fluids are described in U.S. patent application Ser. No. 07/176,923 now abandoned and PCT application U.S. Pat. No. 89/01247, the disclosures of which are incorporated herein by reference. In particular, the applications describe a method of removing aggregated immunoglobulins or immune complexes from a fluid, such as serum, plasma or a diagnostic or therapeutic reagent fluid. The method comprises: contacting the fluid with modified CRP so that the aggregated immunoglobulins or immune complexes bind to the modified CRP; and separating the fluid from the aggregated immunoglobulin or immune complexes bound to the modified CRP.

These applications further describe a method of removing aggregated immunoglobulins or immune complexes from fluids comprising contacting them with an antibody to modified CRP The immune complexes or aggregated immunoglobulin may naturally contain modified CRP, or may be reacted with modified CRP before, or simultaneously with, being contacted with the antibody to modified CRP so that they may be removed from the fluid by the antibody.

Also described is a method of detecting or quantitating immune complexes comprising: contacting the immune complexes with modified CRP so that the immune complexes bind to the modified CRP; and detecting or quantitating the immune complexes bound to the modified CRP by adding a labeled component that binds to the immune complexes or to modified CRP. The labeled component may be antibody to modified CRP.

These applications further describe a method of detecting or quantitating immune complexes comprising contacting them with an antibody to modified CRP. As with the removal method described above, the immune complexes or aggregated immunoglobulin may naturally contain modified CRP, or may be reacted with modified CRP before, or simultaneously with, being contacted with the antibody to modified CRP.

The two applications also describe devices for removing aggregated immunoglobulins or immune complexes from fluids. A suitable device may comprise modified CRP bound to a solid surface and a means for encasing the solid surface or, alternatively, may comprise antibody to modified CRP bound to a solid surface and a means for encasing the solid surface.

The solid surface on which the modified CRP or antibody to modified CRP is immobilized and the encasing means of the device may be any biocompatible material. For instance, the solid surface may be a membraneous surface, agarose-based beads or hollow fibers coated with modified CRP or antibody to modified CRP. The device may be a column packed with beads, a hollow fiber membrane encased in a cylinder like those used in renal dialysis, a microtiter plate containing wells, or any suitable surface, coated with modified CRP or anti-body to modified CRP. The device may also include appropriate tubing for connecting it to a patient and a pump to aid the passage of the fluid through the device and to prevent air from entering the system. The device may be sterilized for therapeutic use, and sterilization may be accomplished in conventional ways such as purging with ethylene oxide or by irradiating the device.

Finally, these two applications describe kits for detecting or quantitating immune complexes. A suitable kit comprises a container holding antibody to modified CRP. Another suitable kit comprises a container holding modified CRP and, optionally, a container of a labeled component that binds to immune complexes or modified CRP to allow the immune complexes to be detected or quantitated. The labeled component may be antibody to modified CRP.

The modified CRP used in the method, kits and devices disclosed in these two applications is the same as the modified CRP described herein Accordingly, the monoclonal antibodies of the present invention directed to epitopes on modified CRP may be used in the methods, kits and devices described in U.S. patent application Ser. No. 07/176,923 and PCT application U.S. Pat. No. 89/01247 wherever it is indicated that antibodies to modified CRP should be used.

The antibodies of the present invention may also be used to purify modified CRP for use in the assays described in these two applications which employ modified CRP. In particular, the mAbs of the present invention may be useful in purifying modified CRP from cell culture supernatants of microorganisms genetically engineered to produced CRP, which as noted above expresses neo-CRP antigenicity. Of course, the mAbs of the present invention having specificity for native CRP may be utilized to purify native CRP.

Methods of purifying antigens with antibodies are well known. For instance, modified CRP or native CRP could be purified by contacting the modified or native CRP with an antibody according to the present invention of the proper specificity. The antibody could be immobilized on a solid surface such as agarose beads and used as a column. Modified or native CRP bound to antibody can be eluted using known means.

Immunoassays for detecting or quantitating native CRP, modified CRP or immune complexes are those known in the art, with the exception stated earlier that solid-phase assays for native CRP must be performed by the ligand capture technique. Such suitable conventional immunoassays that may be used otherwise include competitive assays and immunometric assays. Examples of the latter type are radioimmunometric assays (IRMA) and enzyme-linked immunosorbent assays (ELISA). In a competitive assay, the antigen is labelled with a detectable label. The sample containing the antigen is incubated with the antibody and the labelled antigen, and after formation of immune complexes, separation and detection, the level of antigen in the sample is determined.

In one mode of performing the immunometric assay the antigen is immobilized on a solid phase, e.g., on the surface of microtiter plate wells. The antibody, or an antigen-binding fragment of the antibody is detectably labelled. Incubation of sample with labelled antibody leads to an immobilized antigen-antibody complex and, after separation of unbound antibody, the amount of label is proportional to the amount of antigen.

In another immunometric (sandwich) assay, one antigen-binding antibody is detectably labelled. Another antibody binding the same antigen is immobilized on a solid phase. Incubation of antigen with labelled and immobilized antibody leads to a sandwich and, after separation of unbound antibody, the amount of label is proportional to the amount of antigen. Immunometric assays can be carried out in forward, reverse or simultaneous modes, depending on the order of addition of the immobilized and/or labelled antibodies.

The specific concentrations, the temperature and time of incubation, as well as other assay conditions, can be varied depending on such factors as the concentration of the antigen in the sample, the nature of the sample, and the like. Those skilled in the art will be able to determine operative and optimal assay conditions for each determination while employing routine experimentation.

There are many solid surfaces on which the antigen or antibody can be immobilized and which can be used in the present invention. Suitable solid surfaces are well known and include glass, polystyrene, polypropylene, polyethylene, dextran, nylon, natural and modified celluloses, polymethyl-methacrylate, polycarbonate, polysulfone, polyacrylonitrile, latex beads, polyvinyl alcohol, gels, clay, polyacrylamides and agaroses. Those skilled in the art will know many other suitable solid surfaces for binding, or will be able to ascertain such, using routine experimentation.

Depending on the particular embodiment of the assay of the invention, the antibody or the antigen-binding fragment thereof may be coupled with a detectable label such as an enzyme, radioactive isotope, fluorescent compound or metal, chemiluminescent compound, or bioluminescent compound. Furthermore, the binding of these labels to the desired molecule can be done using standard techniques common to those of ordinary skill in the art.

One of the ways in which the antibody can be detectably labelled is by linking it to an enzyme. This enzyme, in turn, when later exposed to its substrate will react with the substrate in such a manner as to produce a chemical moiety which can be detected by, for example, spectrophotometric or fluorometric means (ELISA system). Examples of enzymes that can be used as detectable labels are horseradish peroxidase, malate dehydrogenase, staphylococcal nuclease, delta-5-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase, and acetylcholine esterase. For increased sensitivity in the ELISA system, the procedures described can be modified using biotinylated antibody reacting with avidin-enzyme conjugates.

The amount of antigen can also be determined by labelling the antibody with a radioactive isotope. The presence of the radioactive isotope would then be determined by such means as the use of a gamma counter or a scintillation counter Isotopes which are particularly useful are $^{3}H$, $^{125}I$, $^{123}I$, $^{32}P$, $^{35}S$, $^{14}C$, $^{51}Cr$, $^{57}Co$, $^{58}Co$, $^{59}Fe$, $^{75}Se$, $^{111}In$, $^{99m}Tc$, $^{67}Ga$, and $^{90}Y$.

Determination of the antigen is also possible by labelling the antibody with a fluorescent compound. When the fluorescently labelled molecule is exposed to light of the proper wavelength, its presence can then be detected due to fluorescence of the dye. Among the most important fluorescent labelling compounds are fluorescein isothiocyanate, rhodamine, phycoerythrin, phycocyanin, allophycocyanin, o-phthaldehyde, and fluorescamine.

Fluorescence emitting metal atoms such as Eu (europium), and other lanthanides, can also be used. These can be attached to the desired molecule by means of metal chelating groups, such as DTPA or EDTA.

Another way in which the antibody can be detectably labelled is by coupling it to a chemiluminescent compound. The presence of the chemiluminescent-tagged immunoglobulin is then determined by detecting the presence of luminescence that arises during the course of a chemical reaction. Examples of particularly useful chemiluminescent labelling compounds are luminol, isoluminol, aromatic acridinium ester, imidazole, acridinium salt, and oxalate ester.

Likewise, a bioluminescent compound may also be used as a label. Bioluminescence is a special type of chemiluminescence which is found in biological systems and in which a catalytic protein increases the efficiency of the chemiluminescent reaction. The presence of a bioluminescent molecule would be determined by detecting the presence of luminescence. Important bioluminescent compounds for purposes of labelling are luciferin, luciferase, and aequorin.

As noted earlier, the invention also comprises kits for the detection or quantitation of native CRP, modified CRP and immune complexes. Such a kit may comprise one or more containers such as bottles, vials, tubes, and the like, each of which contains one of the separate elements to be used in the desired immunoassay method. For example, the kit may comprise a container of unlabeled or detectably labelled mAb according to the present invention of proper specificity. The antibody may be in lyophilized form or in solution or may be immobilized on a solid surface like those described above. Other containers may comprise reagents necessary for determining the amount of labelled antibody or ancillary reagents, such as buffer solutions and standards.

EXAMPLES

EXAMPLE 1: Preparation of Monoclonal Antibodies to CRP

A. Purification of CRP: Human CRP was purified from pleural and ascites fluids by sequential affinity chromatography with PC substituted Biogel, ion exchange chromatography with DE52 and calcium-dependent adsorption chromatography with Biogel A 0.5 m to remove residual serum amyloid P component (SAP) as described in Potempa et al., *Molec. Immunol.*, 20, 1165 (1983). The purified protein was adjusted to 1 mg/ml, dialyzed against TBS-calcium (0.01 M Tris-HCl, 0.15 M NaCl and 0.002 M $CaCl_2$, pH 7.3) with 0.02% (w/v) sodium azide, sterile-filtered and stored at 4° C. Purity of the final CRP preparation was confirmed by radial immunodiffusion analyses for SAP and IgG, Ouchterlony analyses for IgG, IgA, IgM, SAP, fibronectin, Clq, Clr, Cls, C3, ceruloplasmin, albumin and alpha-lipoprotein, and SDS-PAGE analyses as described in Potempa et al., *Molec. Immunol.*, 20, 1165 (1983) and Potempa et al., *Molec. Immunol.*, 24, 531 (1987).

B. Urea, Heat and SDS treatment of CRP: Purified CRP was treated with urea in a slight modification of the method of Potempa et al., *Molec. Immunol.*, 20, 1165 (1983). Briefly, CRP at 1 mg/ml in TBS-calcium was chelated with 0.005 M EDTA and incubated in 8 M ultra-pure urea for 2 hr at 37° C. The urea was removed by dialysis against low ionic strength TBS (0.01 M Tris-HCl and 0.05 M NaCl, pH 7.4), and the soluble CRP preparation obtained is referred to as "urea-CRP".

To prepare "SDS-CRP", CRP in the absence of calcium was incubated in a boiling water bath for 5 min with 0.1% (w/v) SDS.

Heat-treated CRP was prepared by heating CRP at 63° C. for 2 minutes in the absence of calcium to cause denaturation and modification of CRP.

C. Mice: Female 5-6 week old Balb/c mice were obtained from the Jackson Laboratories (Bar Harbor, Me.) or Harlan Sprague Dawley Inc. (Indianapolis, Ind.). Female 5-6 week old RBF/DN mice were obtained from the Jackson Laboratory (Bar Harbor, Me). All mice were housed and maintained in the facilities of the Comparative Research Center of Rush Medical College. Immunizations began at 8-9 weeks of age.

D. Production of Hybridomas: The mAb were produced by standard hybridoma technology using in vivo systemic immunization and polyethylene glycol (PEG) fusion as described in Kennett et al., "Methods for Production and Characterization of Monoclonal Antibodies," in *Monoclonal Antibodies. Hybridomas: A New Dimension In Biological Analysis*, p. 363 (1980). Mice were immunized subcutaneously in the inguinal area with purified immunogen emulsified in an equal volume of complete Freund's adjuvant (CFA) or incomplete Freund's adjuvant (IFA), or emulsified with the RIBI adjuvant system as described by the manufacturer (Ribi Immunochem Research Inc., Hamilton, Mont.). Two intraperitoneal (i.p.) booster immunizations after 2 and 6 weeks were performed using antigen in sterile saline, IFA or RIBI adjuvant. The mice were rested for 2-4 weeks and given a final i.p. injection of 100 μg immunogen/mouse in sterile saline 3 days prior to the fusion.

In fusion 15, unmodified human CRP in the presence of calcium was used as the immunogen with the Freund's adjuvant system in RBF/DN mice. In fusions 13, 21 and 22, a mixture of urea- and heat-modified human CRP expressing neo-CRP determinants was used in Freund's adjuvant for immunization of Balb/c mice. In fusion 26, a combination of urea-CRP and heat-modified rabbit CRP immunogens in the RIBI adjuvant system were injected into Balb/c mice. All immunizations resulted in antibodies to both human native-CRP and neo-CRP specificities, although the response to the immunizing form tended to dominate.

Splenic immune lymphocytes from the immunized mice were fused with the hypoxanthineguanine phosphoribosyltransferase-deficient myeloma FOX-NY (as described in Taggart and Samloff, *Science*, 219, 1228 (1983)) using PEG 1500 (Aldrich Chemical Co. Inc., Milwaukee, Wis.). Hybridomas were selected in the appropriate defined medium (HB101 or HB102; Hana Biologics Inc., Berkeley, Calif.) containing hypoxanthine, aminopterin and thymidine (HAT; Sigma Chemical Co., St. Louis, Mo.) or adenosine, aminopterin and thymidine (AAT; Sigma Chemical Co.), respectively. Antigen-specific clones were screened by direct enzyme linked immunosorbent assay (ELISA) (described below) and cloned at least twice by limiting dilution. Antigen-positive clones were retested for specificity by direct ELISA on plates coated with native CRP, modified CRP (displaying the neo-CRP epitope) and a non-specific control protein (human transferrin, Sigma Chemical Co., or human IgG, Jackson ImmunoResearch Laboratories, Inc., Avondale, PA) and by a ligand capture assay using CRP bound to a PC-KLH coated plate (described below) Stable clones of interest were expanded in vitro in medium supplemented with 2% FCS. The mAb were isotyped by direct ELISA on antigen (i.e., CRP)-coated plates.

E. Culture of Hybridomas: Stable hybridomas were cultured in HB101 or HB102 defined medium with appropriate supplements (Hana Biologics) containing 2% or 5% heat-inactivated fetal calf serum (FCS) (Biologos Inc., Naperville, Ill.), 0.002 M L-glutamine (GIBCO, Grand Island, N.Y.), 100 units/ml penicillin-streptomycin (GIBCO), 0.001 M sodium pyruvate (GIBCO), and $5.5. \times 10^{-5}$ M 2-mercaptoethanol (Sigma Chemical Co.) Viable cells at $2-2.5 \times 10^5$/ml were cultured in plastic culture flasks in a humidified atmosphere at 37° C. in 5% $pCO_2$. For storage, cells ($5 \times 10^6$/ml/vial) were washed, resuspended in HB basal medium containing 20% FCS and 10% dimethyl sulfoxide (DMSO; Fisher Scientific Co., Fairlawn, N.J.) and slow-frozen over liquid nitrogen.

F. Purification of mAb: Immunoglobulin fractions of the mAb were prepared from culture supernatants by precipitation with 50% saturated ammonium sulfate as described in Kennett et al., in *Monoclonal Antibodies. Hybridomas: A New Dimension In Biological Analysis* p. 363 (1980), followed by immediate dialysis into PBS, pH 7.2 (Bacto-FA buffer, Difco Laboratories, Detroit, Mich.). All immunoglobulin preparations were clarified by centrifugation in a Beckman microfuge, made to 0.02% with sodium azide, stored at −70° C. and quantitated using the extinction coefficient of mouse immunoglobulin.

Example 2: Characterization of Monoclonal Antibodies to CRP

The mAbs produced in Example 1 were characterized by ELISA, dot blot and Western blot assays.

A. Reference Antibodies: polyclonal antibodies used in ELISA, dot blot and Western blot assays included unconjugated and horseradish peroxidase (HRP)-conjugated goat anti-mouse IgG plus IgM (H+L) and HRP-conjugated rabbit anti-goat IgG obtained from Pel Freez Biologicals (Rogers, Ark.), and HRP-conjugated avidin obtained from Boehringer Mannheim Biochemicals (Indianapolis, Ind.). The mAb were isotyped using rabbit antiheavy and -light chain isotype-specific reagents obtained from Miles Scientific (Naperville, Ill.), and HRP-conjugated goat anti-rabbit IgG (H+L) obtained from Kirkegaard and Perry Laboratories, Inc. (Gaithersburg, Md.).

The mAb to human CRP obtained from other laboratories included: HD2-4 obtained from the American Type Culture Collection and described in Kilpatrick et al., *Molec Immunol.*, 19, 1159 (1982); EA4-1 obtained from Dr. John E. Volanakis, Dept. of Medicine, University of Alabama in Birmingham (Birmingham, Ala.) and described in Kilpatrick et al., *Molec. Immunol.*, 19, 1159 (1982); and BB-9 from Dr. Richard F. Mortensen, Dept. of Microbiology, Ohio State University (Columbus, Ohio) and described in Tseng et al., *Hybridoma*, 7, 185 (1988).

B. Preparation of PC-KLH: Phosphorylcholine (PC) substituted Keyhole Limpet hemocyanin (PC-KLH) was prepared by incubating KLH (Sigma Chemical Co., St. Louis, Mo.) with para-nitrophenyl phosphorylcholine (Sigma Chemical Co.) diazotized as described by Chesebro and Metzger, *Biochemistry*, 11, 766 (1972). The final derivatization resulted in 28 moles PC per Mr of $1 \times 10^{-5}$ KLH.

C. Biotinylation of CRP: Purified human CRP at 1 mg/ml was incubated with ⅛ volume of NHS-LC-Biotin (Pierce, Rockford, Ill.) at 1 mg/ml for 4 hr at room temperature with occasional mixing. Biotinylated protein was dialyzed at 4° C. for 24 hr against 8 liters of TBS-calcium buffer. The biotinylated CRP preparation showed calcium-dependent binding to PC-KLH, and reacted comparably to unlabeled CRP in the ELISA assays involving anti-native-CRP and anti-neo-CRP mAb.

D. Synthetic CRP Peptides: CRP peptides 1, 2 and 4, synthesized as described in Lindner and Robey, *Int. J. Pept. Protein Res.*, 30. 794 (1987) were generously provided by Dr. F. A. Robey, National Institute of Dental Research, (Bethesda, Md.). Peptide 1 (identical to residues 23-30 of human CRP), peptide 2 (identical to residues 109-123) and peptide 4 (identical to residues 199-206) were prepared to include the tuftsin-like sequences previously identified in the human CRP molecule as described in Osmand et al., *Proc. Nat'l. Acad. Sci. USA*, 74, 1214 (1977); Robey et al., *J. Biol. Chem.*, 262, 7053 (1987). Peptide 3 (identical to residues 137-152 of human CRP) was kindly synthesized and generously provided by Dr. Richard Houghton (Scripps Clinic and Research Foundation, La Jolla, Calif.) to duplicate the amino acid sequence proposed to be involved in the binding of calcium by CRP, See Nguyen et al., *J. Biol. Chem.*, 261, 10450 (1986).

E. Enzyme Linked Immunosorbent Assay (ELISA):

1. Direct ELISA

In the direct ELISA for modified CRP, 50 μl/well of CRP (5 μg/ml) was incubated on polystyrene ELISA plates (Greiner Labortechnik, Germany). Calcium in the CRP solutions was chelated with 0.01 M EDTA in 0.01 M sodium bicarbonate buffer, pH 9.0, prior to coating in order to favor the expression of CRP neoantigenicity on the plate. The wells were washed with VBS (0.05 M veronal, 0.15 M NaCl, pH 7.3) containing 0.05% Tween 20 (v/v) and 0.01 M EDTA (wash buffer) and blocked with 1% BSA (in distilled water) for 30 min at 37° C. The anti-CRP mAb were serially diluted with wash buffer and 50 μl aliquots added to the wells for 30 min at 37° C. followed by washing. Peroxidase-conjugated goat anti-mouse IgG and IgM (H+L) in wash buffer was added to the wells for 30 min at 37° C. After washing, 50 μl ABTS substrate (2-2'azinobis(3-ethylbenzythiazoline-6-sulfonic acid), Sigma Chemical Co.) was added per well for 15 min at room temperature. Plates were read at an absorbance of 414 nm ($A_{414}$) on a Titertek multiscan plate reader (Flow Laboratories, Helsinki, Finland). For the peptide inhibition assays, concentrations of mAb producing half-maximal color change were preincubated with serial dilutions of peptides for 30 min at 37° C. prior to the addition of the mixture to the CRP-coated wells.

2. Ligand Capture ELISA

For the ligand capture ELISA defining "native" CRP, plates were incubated with 50 μl/well of PC-KLH (6.25 μg/ml) in bicarbonate buffer overnight at 4° C., washed with VBS wash buffer and blocked with 1% BSA as described above. After washing, 50 μl/well of CRP (5 μg/ml in VBS-Tween containing 0.002 M $CaCl_2$ was added and incubated for 30 min at 37° C. The mAb, peroxidase-conjugated anti-mouse immunoglobulin reagent and substrate were added as described.

The ligand capture assay identifying the calcium dependence and PC inhibitability of epitope recognition utilized wells coated with polyclonal goat anti-mouse IgG (50 μl at 15 μg/ml in bicarbonate buffer, pH 9.6) and blocked as before. After washing, mAb (50 μl) at a concentration producing half-maximal capture were added and incubated for 30 min at 37° C. Biotinylated CRP (50 μl at $1 \times 10^{-9}$ M (0.02 μg/ml) in VBS-Tween buffer) in the presence of 0.005 M EDTA, 0.002 M CaCl or 0.002 M $CaCl_2$ plus PC (at $10^{-3}$ to $10^{-7}$M) was incubated with the mAb for 30 min at 30° C. Wells were washed and incubated with 50 μl of avidin peroxidase for 30 min at 37° C. and developed with ABTS substrate.

F. Dot blot assays: Following a modification of the procedure of Zhang, *J. Immunol.*, 138. 575 (1987), nitrocellulose membranes (Schleicher & Schuell, Keene, N.H.) were pre-soaked in VBS (pH 7.4) for 30 min, and excess buffer was removed with filter paper and fitted into a Bio-Dot microfiltration apparatus (Bio-Rad). Aliquots (50 μl) of the various test proteins at 5 μg/ml were dotted onto the membrane overnight at 4° C., and vacuum-filtered to remove all the liquid from the wells. Blocking solution (100 μl of 1% BSA) was added to the wells and incubated for 30 min at room temperature (RT), and vacuum-filtered through the membrane. The wells were washed three times with VBS containing 0.05% Tween 20 and 0.002 M $CaCl_2$ (washing buffer). Monoclonal and polyclonal anti-CRP antibodies at concentrations five-fold or more greater than those required for maximal reactivity in the ELISA assays were added for 30 min at RT followed by washing. HRP-conjugated goat anti-mouse IgG and IgM and rabbit anti-goat IgG in washing buffer were incubated for 30 min at RT. Substrate solution (4-chloro-1-naphthol in 10 mM TBS containing methanol and $H_2O_2$) prepared as directed (Bio-Rad, Richmond, Calif.), was added to the wells, and incubation was continued for 30 min at RT for color development.

G. Limited proteolysis of CRP: CRP at 1 mg/ml in TBS was digested with 10% (w/w) Pronase (Calbiochem, San Diego, Calif.) for 3 hr at 37° C. as described in Kinoshita et al., FASEB J.. 2, 1149a (1988). The digest was subjected to FPLC chromatography on a $1 \times 30$ cm Superose 12 gel filtration column (Pharmacia, Piscataway, N.J.) with 0.01 M TBS at a flow rate of 0.3 ml/min. The absorbance at 280 nm of the eluate was continuously monitored, and the peak eluting at the position of pentameric CRP was collected. BioRad gel filtration standard, containing thyroglobulin (670 kDa), immunoglobulin G (158 kDa), ovalbumin (45 kDa), myoglobin (17 kDa) and vitamin $B_{12}$ (1.35 kDa), was used for molecular weight calibration of the FPLC column.

H. Western blot assays: SDS-PAGE was carried out on 13% polyacrylamide minislab gels (BioRad) using the buffer system described by Laemmli, *Nature*, 227, 680 (1970). Protein was transferred to the nitrocellulose membrane using the BioRad Transblot system. The procedure for performing the immunoblot assays was carried out as described for the dot blot assays.

Figure 1E:
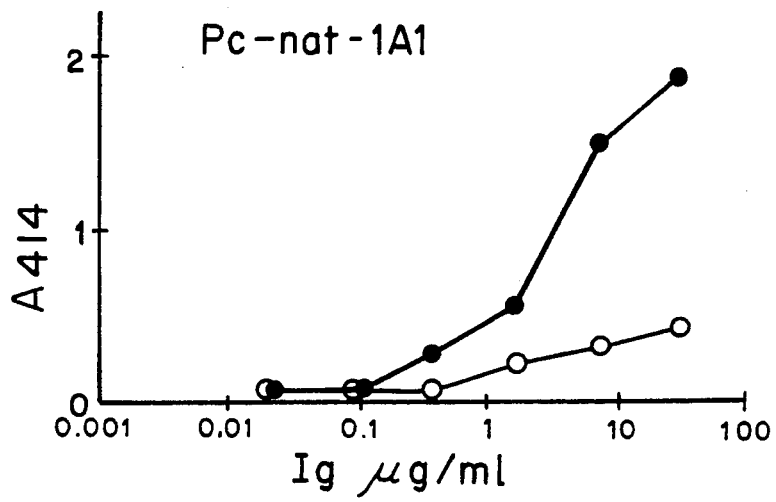
Figure 1F:
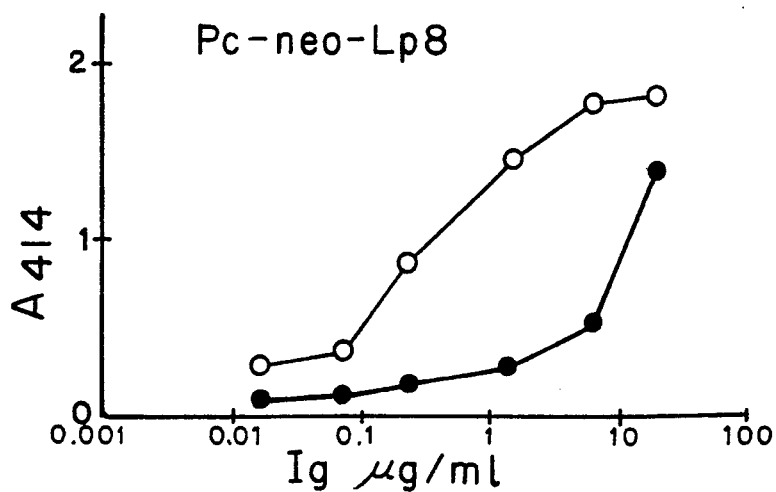

I. Results of ELISA: Seventeen stable mAb were generated against human CRP and first characterized by ELISA for reactivities both with CRP bound to PC-KLH in the presence of calcium (i.e., with "native" CRP epitopes) and with urea-modified CRP in the absence of calcium (i.e., with "neo-CRP" epitopes). Table 1 shows the relative avidity of mAb to these two forms of the molecule on polystyrene plates. Five mAb (designated group I) reacted only with native-CRP; two mAb (designated group II) reacted with both native and modified CRP; and ten mAb (designated groups III and IV) reacted only with modified CRP. FIGS. 1A-1D show the ELISA binding curves of representative mAb of each group, and FIGS. 1E and 1F show the reactivities of polyclonal antisera to native and modified CRP, respectively, for comparison.

The mAb assigned to group I did not react with modified CRP even at concentrations greater than those listed (in general >20 μg/ml), and since as little as 0.07 μg/ml yielded half-maximal activity with native CRP, we concluded that these antibodies had binding specificities exclusively for native CRP epitopes. The group II mAb could bind to both native and modified CRP. However, both mAb reacted more strongly with native CRP. In contrast, the mAb of groups III and IV showed a significant specificity for modified CRP and did not react with ligand-bound native CRP at any concentration tested.

In general, the identification of a native or neo-CRP specificity reflected a >7-fold preferential reactivity with the appropriate native or modified form of CRP. The significantly lower preferential reactivities of mAb 3A1 (group I) and 6A5 (group IV) may reflect technical complications resulting from the use of high concentrations of immunoglobulin in the ELISA assays, a lower affinity of interaction, or a lower stability of antibody in the salting-out procedure.

TABLE 1

Reactivity of Anti-CRP Monoclonal Antibodies With CRP by ELISA

| Antibody | Isotype | ELISA Analyses* Native CRP | ELISA Analyses* Modified CRP |
|---|---|---|---|
| I-15-1D6 | γ2a,k | 0.07 | >20.0 |
| I-26-8D8 | γ1,k | 0.11 | >20.0 |
| I-22-3G12 | γ1,k | 0.21 | >20.0 |
| I-1-4H2 | γ2a,k | 2.50 | >40.0 |
| I-21-3A1 | γ1,k | 24.50 | >40.0 |
| II-15-2C10 | γ2a,k | 0.05 | 3.04 |
| II-26-1A8 | γ1,k | 0.06 | 1.48 |
| III-26-7A8 | γ2b,k | >20.0 | 0.68 |
| III-26-8C10 | γ1,k | >20.0 | 1.59 |
| III-26-6B7 | γ1,k | >20.0 | 1.69 |
| IV-13-3H12 | γ1,k | >20.0 | 0.16 |

TABLE 1-continued

Reactivity of Anti-CRP Monoclonal Antibodies With CRP by ELISA

| Antibody | Isotype | ELISA Analyses* Native CRP | ELISA Analyses* Modified CRP |
|---|---|---|---|
| IV-26-2H5 | γ1,k | >20.0 | 0.16 |
| IV-26-9C9 | γ1,k | >20.0 | 0.21 |
| IV-15-3G8 | γ1,k | >20.0 | 0.26 |
| IV-26-7C6 | γ1,k | >20.0 | 0.41 |
| IV-13-12D7 | γ2a,k | >20.0 | 0.90 |
| IV-26-6A5 | γ1,k | >514.00 | 257.00 |
| Goat anti-native CRP | | 1.88 | >20.00 |
| Goat anti-neo-CRP | | 8.75 | 0.39 |

*Values indicate μg/ml mAb IgG required for half-maximal reactivity in ELISA assays.

J. Reactivity of mAb with Pronase-digested fragments of CRP: To further characterize the CRP epitopes reactive with the mAb, CRP was partially digested with Pronase, and the fragments were evaluated for reactivity with the various antibodies by Western blot analysis Limited Pronase digestion results in two fragments identifiable in SDS gels with molecular weights on gel filtration FPLC of 16 kD and 6.5 kD, designated fragments A and B respectively, and containing the amino and carboxy terminals of the molecule, respectively. Fragment A consists of residues 1-146 and/or an additional breakdown product 10 residues shorter (this mixture is referred to as "fragment A" or "residues 1-146" herein). Fragment B consists of residues 147-206 (Kinoshita et al., FASEB J., 2, 1149a (1988); Kinoshita et al. submitted for publication).

Figure 2:
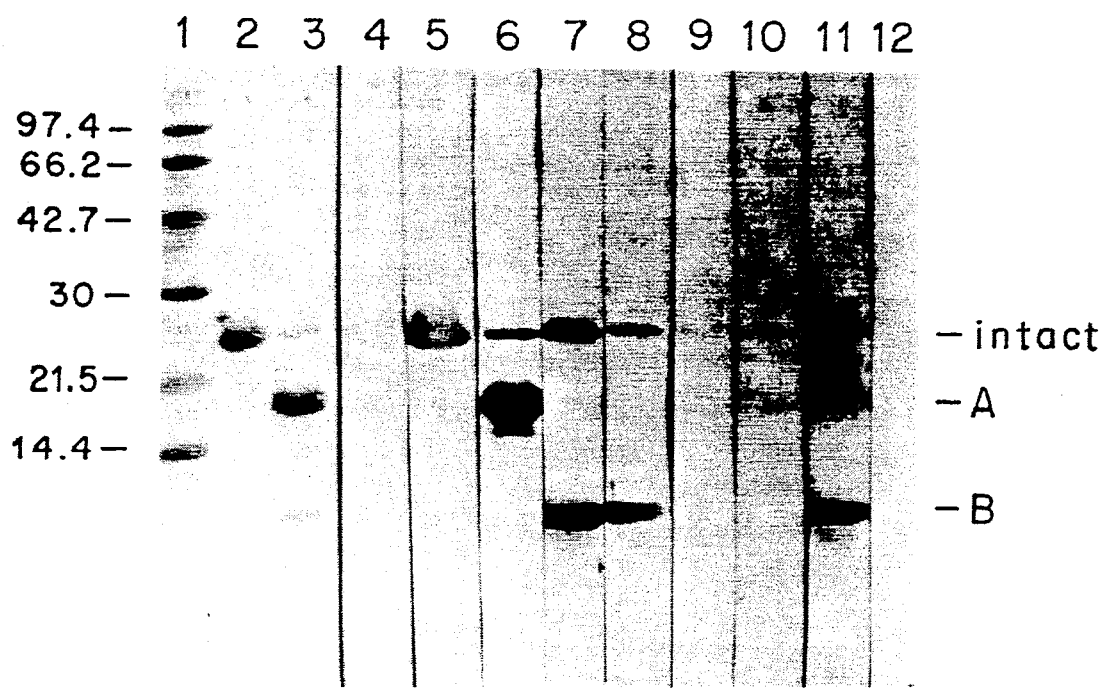
FIG. 2. Western blot analysis of CRP in SDS-PAGE using mAb. Protein blots in the first three lanes (lane 1, standards; lane 2, CRP; and lane 3, Pronase-treated CRP) were stained with Amido Black directly with no blocking, while in the other lanes, the mAb were incubated with the blots after blocking. Lane 4 was incubated with mAb 1D6; lane 5 with mAb 2C10; lane 6 with mAb 6B7; lane 7 with mAb 3H12; lane 8 with mAb 6A5; lane 9 with mouse Ig control; lane 10 with goat polyclonal anti native CRP 1A1; lane 11 with goat polyclonal antineo-CRP LP8; and lane 12 with the goat Ig control.

Three bands were visible on Western blots of the Pronase-treated CRP stained with amido black (FIG. 2, lane 3). The slowest migrating band corresponded to the intact CRP subunit (apparent molecular weight 23 kDa), the second band to fragment A and the third band to fragment B (FIG. 2, top to bottom). The results are summarized in Table 2, with the Western blot patterns of representative mAb from each of the groups shown in FIG. 2.

TABLE 2

Reactivity of Anti-CRP Monoclonal Antibodies with CRP Fragments By Western Blot Assays

| Antibody | Western Blots # (Pronase-treated CRP) Intact Subunit (22.5 kDa) | Fragment A (16 kDa) | Fragment B (6.5 kDa) |
|---|---|---|---|
| I-15-1D6 | — | — | — |
| I-26-8D8 | — | — | — |
| I-22-3G12 | — | — | — |
| I-1-4H2 | — | — | — |
| I-21-3A1 | — | — | — |
| II-15-2C10 | + | — | — |
| II-26-1A8 | + | — | — |
| III-26-7A8 | + | + | — |
| III-26-8C10 | + | + | — |
| III-26-6B7 | + | + | — |
| IV-13-3H12 | + | — | + |
| IV-26-2H5 | + | — | + |
| IV-26-9C9 | + | — | + |
| IV-15-3G8 | + | — | + |
| IV-26-7C6 | + | — | + |
| IV-13-12D7 | + | — | + |
| IV-26-6A5 | + | — | + |
| Goat anti-native CRP | — | — | — |
| Goat anti-neo- | + | + | + |

TABLE 2-continued

Reactivity of Anti-CRP Monoclonal Antibodies with CRP Fragments By Western Blot Assays

| Antibody | Western Blots # (Pronase-treated CRP) | | |
|---|---|---|---|
| | Intact Subunit (22.5 kDa) | Fragment A (16 kDa) | Fragment B (6.5 kDa) |
| CRP | | | |

Western blot/SDS-PAGE analysis of Pronase-treated CRP, using the mAb at concentrations at least 5-fold greater than those required for maximal reactivity in the ELISA assays.

The group I mAb, did not react with any band on the Western blots The group II mAb reacted with the intact CRP subunit, but not with either fragment A or B. The group III mAb reacted with the intact CRP subunit and fragment A (residues 1–146), while the group IV mAb reacted with the CRP subunit and fragment B (residues 147–206). These results provided the basis for distinguishing group III and group IV mAb from each other. Thus, together with the determinant recognized by the group II mAb, there are at least three epitopes (i.e., two neo-CRP and one native CRP determinant) expressed on the modified CRP molecule Polyclonal antibody to native CRP did not react with any band on the SDS gels while polyclonal anti-neo-CRP reacted with all three bands, emphasizing that this latter antibody is comprised of at least two different anti-neo-CRP specificities.

K. Further characterization of the mAb by dot blot analysis: To further evaluate the grouping of the anti-native and anti-neo-CRP mAb defined by ELISA and Western blot analyses, the mAb were reacted with various molecular forms of CRP in a series of dot blot assays on nitrocellulose. The forms used included native CRP in the presence of calcium but not bound to PC-KLH, and reagent-modified CRP (urea-CRP and SDS-CRP) expressing neo-CRP epitopes in absence of adsorption onto polystyrene. The related pentraxin SAP and the serum proteins human IgG and transferrin were used as specificity controls. The results are shown in Table 3.

Exactly as in the ELISA assays, group I mAb (ID6, 8D8, 3G12, 4H2 and 3A1) reacted only with native CRP and not with the modified forms (Table 3). Group II mAb (2C10 and 1A8) reacted with both native and modified CRP. The remaining mAb (groups III and IV) reacted only with urea- or SDS-modified CRP but not with native CRP either in the presence or absence of calcium.

TABLE 3

Reactivity of Anti-CRP Monoclonal Antibodies with Intact CRP and CRP Peptides by Dot Blot Analysis

| Antibody* | Native CRP | SDS-CRP | Urea-CRP | CRP Peptides | | | | SAP |
|---|---|---|---|---|---|---|---|---|
| | | | | 1 | 2 | 3 | 4 | |
| I-15-1D6 | + | − | − | − | − | − | − | − |
| I-26-8D8 | + | − | − | − | − | − | − | − |
| I-22-3G12 | + | − | − | − | − | − | − | − |
| I-1-4H2 | + | − | − | − | − | − | − | − |
| I-21-3A1 | + | − | − | − | − | − | − | − |
| II-15-2C10 | + | + | + | − | − | − | − | − |
| II-26-1A8 | + | + | + | − | − | − | − | − |
| III-26-7A8 | − | + | + | − | − | − | − | − |
| III-26-8C10 | − | + | + | − | − | − | − | − |
| III-26-6B7 | − | + | + | − | − | − | − | − |
| IV-13-3H12 | − | + | + | − | − | − | + | − |
| IV-26-9C9 | − | + | + | − | − | − | + | − |
| IV-26-2H5 | − | + | + | − | − | − | + | − |
| IV-15-3G8 | − | + | + | − | − | − | + | − |
| IV-26-7C6# | | | | | | | | |
| IV-13-12D7 | .− | + | + | − | − | − | + | − |
| IV-26-6A5# | | | | | | | | |
| Goat anti-native CRP | + | − | − | − | − | − | − | − |
| Goat anti-neo-CRP | − | + | + | − | − | − | − | − |

*The mAb were used at concentrations at least 5-fold greater than those required for maximal reactivity in the ELISA assays.
Group IV mAb 26-7C6 and 26-6A5 could not be tested, because of high background reactivity with nitrocellulose.

L. Reactivity of mAb with synthetic CRP peptides: For more precise mapping of CRP epitopes, the mAb were tested for reactivity with four synthetic CRP peptides, first by dot blot analysis The results are shown in Table 3. Five of the mAb which bound to fragment B (3H12, 9C9, 2H5, 3G8 and 12D7) displayed reactivity with the C-terminal octapeptide of CRP (peptide 4). The other two mAb of group IV (7C6 and 6A5) could not be evaluated by this assay because of background reactivity. Peptides 1, 2 and 3 were not recognized by any of the mAb.

To further elaborate on the specificity for peptide 4, the ability of the terminal octapeptide to inhibit the binding of the mAb to CRP was evaluated by ELISA. All the mAb which reacted with peptide 4 by dot blot analysis were inhibited by the peptide in these ELISA analyses. The binding of 7C6 to CRP also was inhibited completely by peptide 4 while the interaction of 6A5 was not.

Figure 3:
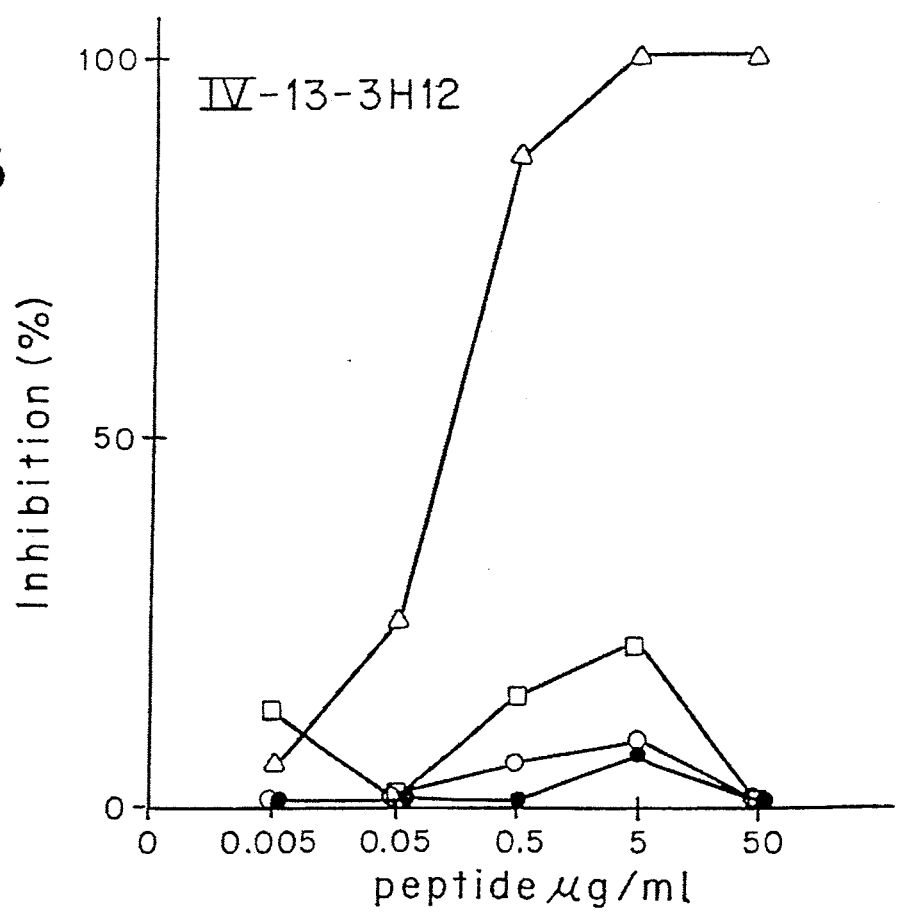
FIG. 3. Inhibition of the binding of mAb 3H12 to immobilized CRP by synthetic peptides using ELISA analysis. Peptide 1 (●) is identical; to CRP residues 23-30; peptide 2 () is identical to CRP residues 109-123; peptide 3 (□) is identical to CRP residues 137-152; and peptide 4 (Δ) is identical to CRP residues 199-206.

FIG. 3 shows the inhibition curve of the binding of a representative group IV mAb (3H12) by peptide 4, and the lack of inhibition by peptides 1–3. Whether the inability to demonstrate a reactivity of mAb 6A5 with peptide 4 by direct binding or peptide inhibition reflected a real specificity difference or another factor, such as its apparent lower titer or a low affinity, is not yet clear.

M. Characterization of mAb to human CRP obtained from other laboratories: Previously reported mAb to human CRP were obtained from other laboratories and tested for reactivity with both native and modified CRP. These included HD2-4, a calcium-independent mAb which lacks anti-PC idiotype activity, and EA4-1 and BB-9, which both are calcium-dependent antibodies with anti-PC idiotype reactivity. Results of ELISA, dot blot and Western blot analyses are shown in Table 4. HD2-4 displayed anti-native CRP reactivities indistinguishable from those of the group I mAb, while BB-9 and EA4-1 exhibited both anti-native and anti-neo-CRP reactivities in a pattern characteristic of Group II antibodies.

TABLE 4

Categorization of Anti-CRP mAb Prepared in Other Laboratories#

| Antibody | Isotype | ELISA Reactivity* | | Western Blots Pronase-treated CRP | | | Dot Blot Analyses | | |
|---|---|---|---|---|---|---|---|---|---|
| | | Native CRP | Modfd CRP | Intact Subunt | Frg A | Frg B | Nat CRP | SDS-CRP | Urea-CRP |
| JEV-HD2-4# | gamma-2a,k | 0.44 | >8.85 | − | − | − | + | − | − |
| RFM-BB9-2# | gamma-1,k | 12.50 | 100.00 | + | − | − | + | + | + |
| JEV-EA4-1# | gamma-1,k | 2.5 | 1.5 | + | − | − | + | + | + |

Kindly provided by Drs. John E. Volanakis and Richard F. Mortensen.
*Values indicate the micrograms/ml antibody required to yield half-maximal reactivity.

N. Calcium dependence and PC inhibitability of epitopes reactive with the mAb: The effects of calcium and phosphorylcholine (PC) on the reactivity of the mAb with fluid phase CRP were tested by a capture ELISA, which measured their ability to bind biotinylated CRP when the mAb was immobilized on the assay plates coated with goat anti-mouse IgG. The results are shown in Table 5.

TABLE 5

Effect of Calcium on the Reactivity of Anti-CRP Monoclonal Antibodies with CRP*

| Antibody | CRP in Calcium | CRP in EDTA | % change |
|---|---|---|---|
| I-5-1D6 | 0.759 | 0.258 | −66% |
| I-26-8D8 | 0.253 | 0.288 | <15% |
| I-22-3G12 | 1.049 | 0.816 | −22% |
| I-1-4H2 | 0.248 | 0.000 | −100% |
| I-21-3A1 | 0.195 | 0.885 | +454% |
| JEV-HD2-4 | 0.888 | 0.813 | <15% |
| II-15-2C10 | 1.620 | 1.443 | <15% |
| II-26-1A8 | 1.541 | 1.482 | <15% |
| JEV-EA4-1 | 0.918 | <0.002 | −100% |
| III-26-7A8 | 0.018 | 0.022 | |
| III-26-8C10 | 0.007 | <0.002 | |
| III-26-6B7 | 0.062 | 0.069 | |
| IV-13-3H12 | <0.002 | 0.008 | |
| IV-26-2H5 | <0.002 | 0.017 | |
| IV-26-9C9 | 0.033 | 0.002 | |
| IV-15-3G8 | 0.015 | 0.011 | |
| IV-26-7C6 | <0.002 | <0.002 | |
| IV-13-12D7 | <0.002 | <0.002 | |
| IV-26-6A5 | <0.002 | <0.002 | |

*Reactivity of polystyrene-immobilized mAb with biotinylated CRP in the presence of 0.002M CaCl$_2$ or 0.005M EDTA. The values represent A$_{414}$ at the concentration of mAb which showed half-maximal binding of biotinylated CRP.

All the group I and II anti-native-CRP mAb bound fluid phase CRP in the presence of calcium. However, the reactivities of CRP with most of these antibodies were significantly influenced by the concentration of calcium available. The reactivities of three of the group I antibodies with CRP were reduced in the presence of EDTA (4H2, 1D6 and 3G12 by 100%, 66% and 22%, respectively), that of 3A1 was enhanced approximately four-fold, while that of 8D8 was not affected at all (<15% change). Four of the group I mAb could, therefore, be described as recognizing calcium-dependent or calcium-influenced epitopes. The binding of the group II antibodies 2C10 and 1A8 was not significantly changed when reacted with CRP in the presence of EDTA. The reactivities of the previously reported calcium-independent mAb HD2-4 and calcium-dependent mAb EA4-1 are shown for comparison. No anti-neo-CRP mAb, either from group III or group IV, was able to bind fluid phase native CRP in the presence of either calcium or EDTA.

Figure 4:
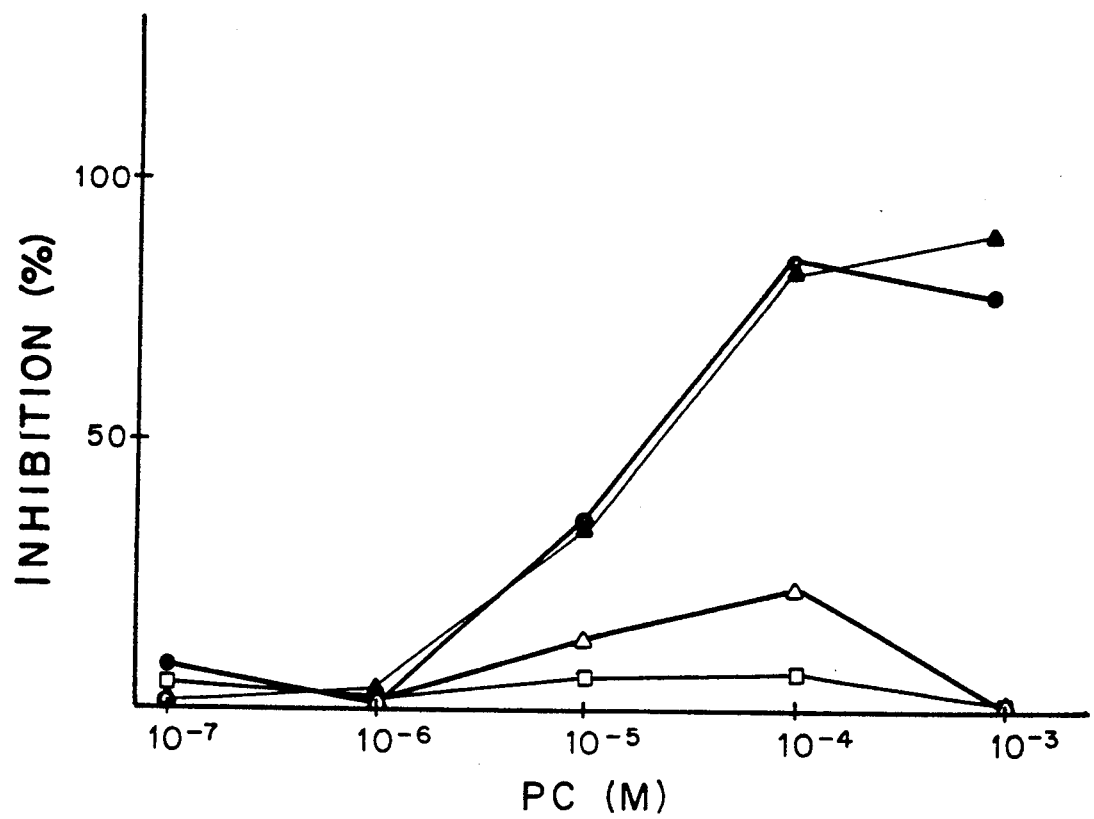
FIG. 4. Phosphorylcholine (PC) inhibition of the binding of biotinylated CRP to mAb. The mAb were used at concentrations giving 25-50% maximal color change. Biotinylated CRP was added at a concentration of $1 \times 10^{-9}$ M. The effects of increasing concentrations of PC on mAb 4H2 (●), JEV-EA4-1, (▲), 15-2C10 (□) and JEV-HD2-4 (Δ) are shown.

The interactions of the group I and II mAb with CRP in the presence of calcium were tested for inhibitability by PC. FIG. 4 shows inhibition data using representative mAb. Of the mAb reported in this paper, only mAb 4H2, which had shown absolute calcium dependence in the assay utilized above, was inhibited by PC. The reactivity of mAb EA4-1, a known PC-inhibitable mAb tested for comparison, was similarly inhibited by PC.

O. Cross-Reactivity With Rabbit CRP And SAP

Before amino acid sequence data confirmed the highly conserved homologies among the C-reactive proteins of different species, serologic evidence showed extensive immunologic cross-reactivities between the C-reactive proteins of different species. Certain antisera to human CRP cross-reacted with rabbit, monkey, chicken, dog, horse, mouse, guinea pig and rat acute phase serum proteins (reviewed in Baltz et al., *Ann. N. Y. Acad. Sci.*, 273, 49 (1982)). Nilsson utilized comparative Ouchterlony analyses to identify three antigenic determinants on human CRP: one determinant found only on human CRP; one found on human and monkey, but not on rabbit CRP; and one shared by human, monkey and rabbit proteins. See Nilsson, *Int. Arch. Allergy*, 32, 545 (1967). More recently, Rees et al., *Clin. Immunol. Immunopathol.*, 48, 95 (1988) showed that a polyclonal antibody reactive with human neo-CRP, but not with native CRP, determinants cross-reacted with modified rabbit CRP.

Some mAbs described herein, while selected for reactivity with human native- and neo-CRP epitopes, did show some cross-reactivity with rabbit CRP. Preliminary studies with selected mAb showed that the group I mAb 8D8 cross-reacted with native rabbit CRP. Other group I specificities (e.g., 1D6 and 4H2) were directed to human CRP only. Group II, III and IV mAb with antineo-CRP reactivities (2C10, 6B7, 7A8, 3H12 and 9C9 were tested) cross-reacted significantly with modified rabbit CRP in appropriate ELISA and Western blot analyses, suggesting that the anti-neo-CRP mAb might be useful in phylogenetic investigations of C-reactive proteins generally. Furthermore, the group III and IV mAb tested mapped to similar Pronase-generated fragments on rabbit as well as human CRP.

Despite the high degree of homology between human CRP and human SAP (see Osmand et al., *Proc. Natl. Acad. Sci. USA.* 74, 739 (1977); Lei et al., *J. Biol. Chem.*, 260, 13377 (1985); Woo et al., *J. Biol. Chem.*, 260, 13384 (1985)), none of the mAb described herein reacted with SAP. A similar lack of cross reactivity had been reported with polyclonal antibodies raised to these molecules, Maudsley and Pepys, *Immunology*, 62, 17 (1987). However, the results described herein were limited by the immunization and screening procedures used.

P. Summary Of Results: The mAb presented herein were divided into four groups based upon the reactivities observed All the anti-native human CRP mAb (groups I and II) showed reactivity with both ligand-associated and free (i.e., native) CRP in the presence of calcium. However, the group I anti-native mAb did not react with CRP modified in the absence of calcium and did not detect CRP subunits in SDS-PAGE The group II mAb showed significant, although reduced, reactivity with neo-CRP determinants in the absence of calcium but readily detected CRP subunits in SDS-PAGE. The group III and IV mAb did not react with native CRP either in the presence of absence of calcium, but reacted strongly with the modified forms of CRP. These results suggest that epitopes recognized by group I mAb are conformational and discontinuous in amino acid sequence, while epitopes recognized by group II, III and IV mAb probably are comprised of continuous amino acid sequences which are not exposed or expressed until the molecule is unfolded or modified in certain other ways.

CRP is a calcium-binding protein with one or two calcium binding sites per subunit (Gotschlich and Edelman, *Proc. Natl. Acad. Sci. USA*, 57, 706 (1967). Removal of calcium from CRP produces a detectable change in the circular dichroism spectrum of CRP, Young and Williams, *J. Immunol.*, 121, 1893 (1978). The importance of calcium to the reactivity of CRP with certain antibodies was demonstrated by Volanakis and his colleagues (see Kilpatrick et al., *Molec. Immunol.*, 19, 1159 (1982); Volanakis et al., *J. Exp. Med.*, 153, 1604 (1981)) who described calcium-dependent, PC-inhibitable, as well as calcium-independent, mAb reactivities. Our capture assay clarifying the influence of calcium on epitope recognition by anti-native CRP mAb identified two types of calcium dependence. They were an enhanced reactivity in the presence of calcium and an enhanced reactivity in the presence of EDTA. Of importance is the fact that all the calcium-influenced epitopes involved in reactivities with the mAb described herein were native-and not neo-CRP determinants and reacted with mAb assigned to group I. However, one of the five group I antibodies and both of the group II antibodies reacted with epitopes which were not influenced by the presence or absence of calcium. The mAb which displayed the greatest dependence on calcium (4H2) also was inhibited by PC, suggesting that, like the mAb described by Kilpatrick et al., *Molec. Immunol.*, 19, 1159 (1982), this mAb has "anti-idiotype" reactivity with the PC-binding site of CRP.

A summary of the data with our mAb suggest that there are at least four epitopes detectable on native human CRP by the group I mAb: 1) a calcium-dependent, PC-inhibitable idiotope identified by mAb 4H2; 2) a calcium-dependent, non-PC-inhibitable epitope identified by mAb ID6; 3) a calcium-influenced, EDTA-enhanced epitope identified by mAb 3A1; and 4) a calcium-independent epitope identified by mAb 8D8 which also displays a unique cross reactivity with rabbit CRP. The group II mAb (i.e., 2C10 and 1A8) recognize a fifth native CRP epitope, which unlike the other four, is retained as the molecule is altered by the various treatments.

Neo-CRP epitopes were defined using CRP modified in the absence of calcium by immobilization onto plastic, by urea or SDS treatments or by limited digestion with Pronase, and further localized utilizing synthetic CRP peptides. Although neo-CRP epitope expression had been shown in previous studies principally to require a modification in the absence of calcium (see Potempa et al., *Molec. Immunol.*, 20, 1165 (1983); Potempa et al., *Molec. Immunol.*, 24, 53, (1987)), immobilization of CRP on polystyrene ELISA plates in the presence or absence of calcium resulted in equivalent expression of antineo-CRP epitopes. In addition, the antibody capture assay showed that chelation of fluid phase CRP alone did not lead to the expression of neo-CRP epitopes. The absence of calcium may favor the modifications which expose neo-CRP epitopes, such as urea, heat and protease treatments, but neo-CRP expression itself does not appear to be dependent on either the presence or absence of calcium.

Antibodies to neo-CRP epitopes which are not expressed on fluid phase or PC-bound CRP in the presence of calcium, but are expressed by urea- and SDS-modified CRP, react with the CRP subunit and Pronase-generated fragments of CRP on Western blots. The group III antineo-CRP reactivity was localized to residues 1–146 of the CRP subunit (fragment A of the Pronase digest), while reactivity of the group IV mAb was localized to residues 147–206 of the CRP subunit (fragment B of the Pronase digest) and predominantly to the C-terminal octapeptide of CRP. The data indicate that there are minimally two neo-CRP epitopes expressed only on modified CRP conformations and at least one epitope seen on native CRp which is retained after the various modifications.

EXAMPLE 3: Assays Of Normal And Acute Phase Sera

Studies with representative mAb in serum protein electrophoresis and immunofixation analyses of normal and acute phase sera showed that group I and II anti-native CRP mAb (1D6, 8D8 and 2C10) can detect CRP in acute phase sera at concentrations of >8 μg/ml. No significant interactions were seen in this small (fifteen patients), random sampling of sera with the anti-neo-CRP mAb from Groups III or IV. The results with mAb 2C10 suggest that the report of anti-neo-CRP reactivity in acute phase serum by Potempa et al., *Molec. Immunol.*, 24, 531 (1987) could have been due to an antibody with a group II-type of specificity in the polyclonal reagent, i.e. to a native-CRP epitope retained on the modified forms, and may not be indicative of a newly expressed neo-CRP determinant.

EXAMPLE 4: Immunohistochemical Assays

Investigations also confirm the applicability of the mAb to the immunohistochemical localization of CRP. Representative anti-neo-CRP mAb (8C10 and 3H12) as well as anti-native mAb (1D6 and 8D8) reacted with frozen sections of certain human liver specimens suggesting that both native CRP and neo-CRP specificities are naturally occurring.

We anticipate that the mAb defined herein will be important tools for identifying neo-CRP epitopes in vivo and for structure-function mapping of complement and cell-activating properties of the CRP molecule.

Deposit Of Hybridomas: Four hybridomas, the preferred one from each of the four groups identified herein, were deposited at the American Type Culture Collection (ATCC) on Jun. 29, 1989. The four were:

| Designation Used Herein | ATCC Accession No. |
| --- | --- |
| I-15-1D6 | HB 10178 |
| II-15-2C10 | HB 10175 |
| III-26-8C10 | HB 10176 |
| IV-13-3H12 | HB 10177 |

We claim:

1. A monoclonal antibody which binds to C-reactive protein (CRP) and which has the following specificities:
   a) reacts with native human CRP;
   b) does not react with modified human CRP;
   c) does not react with intact human CRP subunit;
   d) does not react with fragment A of human CRP;
   e) does not react with fragment B of human CRP;
   f) does not react with CRP peptides 1 (residues 23-30 of human CRP), 2 (residues 109-123 of human CRP), 3 (residues 137-152 of human CRP) or 4 (residues 199-206 of human CRP);
   g) does not react with serum amyloid P component;
   h) recognizes a calcium-dependent epitope on native human CRP; and
   i) its reactivity with native human CRP is not inhibited by phosphorylcholine.

2. A monoclonal antibody which binds to C-reactive protein (CRP) and which has the following specificities:
   a) reacts with native human CRP;
   b) reacts with modified human CRP;
   c) reacts with intact human CRP subunit;
   d) does not react with fragment A of human CRP;
   e) does not react with fragment B of human CRP;
   f) recognizes a calcium-independent epitope on native human CRP;
   g) its reactivity with native human CRP is not inhibited by phosphorylcholine;
   h) does not react with CRP peptides 1 (residues 23-30 of human CRP), 2 (residues 109-123 of human CRP), 3 (residues 137-152 of human CRP) or 4 (residues 199-206 of human CRP); and
   i) does not react with serum amyloid P component;
   the monoclonal antibody having been produced by immunizing an animal with an immunogen selected from the group consisting of native human CRP, modified human CRP and the combination of modified human CRP and modified rabbit CRP.

3. A monoclonal antibody which binds to C-reactive protein (CRP) and which has the following specificities:
   a) does not react with native human CRP;
   b) reacts with modified human CRP;
   c) reacts with intact human CRP subunit;
   d) reacts with fragment A of human CRP;
   e) does not react with fragment B of human CRP;
   f) does not react with CRP peptides 1 (residues 23-30 of human CRP), 2 (residues 109-123 of human CRP), 3 (residues 137-152 of human CRP) or 4 (residues 199-206 of human CRP);
   g) is not able to bind fluid phase native human CRP in the presence of absence of calcium; and
   h) does not react with serum amyloid P component.

4. A monoclonal antibody according to claim 3 which has the further specificity:
   i) reacts with modified rabbit CRP.

5. A monoclonal antibody which binds to C-reactive protein (CRP) and which has the following specificities:
   a) does not react with native human CRP;
   b) reacts with modified human CRP;
   c) reacts with intact human CRP subunit;
   d) does not react with fragment A of human CRP;
   e) reacts with fragment B of human CRP;
   f) does not react with CRP peptides 1 (residues 23-30 of human CRP), 2 (residues 109-123 of human CRP), or 3 (residues 137-152 of human CRP);
   g) is not able to bind fluid phase native human CRP in the presence of absence of calcium; and
   h) does not react with serum amyloid P component.

6. A monoclonal antibody according to claim 10 which has the further specificity:
   i) reacts with modified rabbit CRP.

7. A monoclonal antibody according to claim 5 which has the further specificity that it reacts with CRP peptide 4 (residues 199-206 of human CRP).

8. A hybridoma capable of producing a monoclonal antibody according to claim 1.

9. An immunoassay for detecting or quantifying native C-reactive protein (CRP) comprising contacting a sample containing native CRP with a monoclonal antibody according to claim 1.

10. An immunoassay for detecting or quantifying modified C-reactive protein (CRP) comprising contacting a sample containing modified CRP with a monoclonal antibody according to any one of claims 3-7.

11. A kit for performing an immunoassay for native C-reactive protein comprising a container of a monoclonal antibody according to claim 1.

12. A kit for performing an immunoassay for modified C-reactive protein comprising a container of a monoclonal antibody according to any one of claims 3-7.

13. A hybridoma capable of producing a monoclonal antibody according to claim 2.

14. A hybridoma capable of producing a monoclonal antibody according to any one of claims 3-7.

15. An immunoassay for detecting or quantifying native C-reactive protein (CRP) or modified CRP comprising contacting a sample containing native or modified CRP with a monoclonal antibody according to claim 2.

16. A kit for performing an immunoassay for native C-reactive protein (CRP) or modified CRP comprising a container of monoclonal antibody according to claim 3.

* * * * *

UNITED STATES PATENT AND TRADEMARK OFFICE
CERTIFICATE OF CORRECTION

PATENT NO. : 5,272,258
DATED : December 21, 1993
INVENTOR(S) : Joan N. Siegel et al.

It is certified that error appears in the above-indentified patent and that said Letters Patent is hereby corrected as shown below:

On the Title Page, item [63]

In column 1, line 11, delete "Dec. 7" and substitute --June 27--.

In column 1, line 23, after "vitro" delete "." and substitute --,--.

In column 1, line 40, after "Med." insert --,--.

In column 1, line 42, after "Immunol" insert --.--.

In column 1, line 46, after "plates" insert --.--.

In column 1, line 47, delete "anti-genicty" and substitute --antigenicity--.

In column 2, line 2, after "Inflammation" delete "." and substitute --,--.

In column 2, line 7, after "Immunol" insert --.--.

In column 2, line 12, after "Immunol" insert --.--.

In column 2, line 17, delete "CRF" and substitute --CRP--.

UNITED STATES PATENT AND TRADEMARK OFFICE
CERTIFICATE OF CORRECTION

PATENT NO. : 5,272,258
DATED : December 21, 1993
INVENTOR(S) : Joan N. Siegel et al.

It is certified that error appears in the above-indentified patent and that said Letters Patent is hereby corrected as shown below:

In column 2, line 20, after "Biochem" insert --.--.

In column 2, line 34, after "34" insert --,--.

In column 2, line 41, after "Fluids" insert --,--.

In column 3, line 64, after "sub-unit;" insert a new paragraph.

In column 4, line 43, delete "0" and substitute --(O)--.

In column 4, line 53, delete "ID6" and substitute --1D6--.

In column 4, line 61, after "identical" delete --;--.

In column 4, line 62, delete "0" and substitute --(O)--.

UNITED STATES PATENT AND TRADEMARK OFFICE
CERTIFICATE OF CORRECTION

PATENT NO. : 5,272,258
DATED : December 21, 1993
INVENTOR(S) : Joan N. Siegel et al.

It is certified that error appears in the above-indentified patent and that said Letters Patent is hereby corrected as shown below:

In column 5, line 9, after "be" delete ".".

In column 5, line 50, after "CRP" insert --,--.

In column 6, line 41, after "herein" insert --,--.

In column 10, line 24, after "below)" insert --,--.

In column 10, line 36, after "Co.)" insert --,--.

In column 11, line 36, after "30" delete "." and substitute --,--.

In column 12, line 32, delete the first occurrence of "CaCl" and substitute --CaCl$_2$--.

In column 12, line 38, after "138" delete "." and substitute --,--.

In column 12, line 65, delete "J.." and substitute --J.,--.

In column 12, line 65, before "The" insert --Pronase is a mixture of proteases obtained from Streptomyces griseus.--.

In column 14, line 23, after "analysis" insert --,--.

UNITED STATES PATENT AND TRADEMARK OFFICE
CERTIFICATE OF CORRECTION

PATENT NO. : 5,272,258
DATED : December 21, 1993
INVENTOR(S) : Joan N. Siegel et al.

It is certified that error appears in the above-indentified patent and that said Letters Patent is hereby corrected as shown below:

In column 15, line 16, after "blots" insert --.--.

In column 16, line 28, after "analysis" insert --.--.

In column 18, line 65, after "observed" insert --.--.

In column 19, line 2, after "SDS-PAGE" insert --.--.

In column 20, line 22, delete "CRp" and substitute --CRP--.

In claim 3, line 13, delete the first occurrence of "of" and substitute --or--.

In claim 5, line 12, delete the first occurrence of "of" and substitute --or--.

UNITED STATES PATENT AND TRADEMARK OFFICE
CERTIFICATE OF CORRECTION

PATENT NO. : 5,272,258
DATED : December 21, 1993
INVENTOR(S) : Joan N. Siegel et al.

It is certified that error appears in the above-indentified patent and that said Letters Patent is hereby corrected as shown below:

In claim 6, line 1, delete "10" and substitute --5--.

In claim 16, line 4, delete "3" and substitute --2--.

Signed and Sealed this

Eighth Day of April, 1997

Attest:

BRUCE LEHMAN

Attesting Officer

Commissioner of Patents and Trademarks